United States Patent [19]

Schmitz-Josten et al.

[11] 4,437,836
[45] Mar. 20, 1984

[54] PHOTOPOLYMERIZABLE DENTAL COMPOSITIONS

[75] Inventors: Robert Schmitz-Josten, Cologne; Carlhans Süling, Odenthal; Wolfgang Podszun, Cologne; Bruno Bömer, Leverkusen; Manfred Borgardt, Wuppertal; Michael Walkowiak, Leverkusen, all of Fed. Rep. of Germany

[73] Assignee: Bayer Aktiengesellschaft, Leverkusen, Fed. Rep. of Germany

[21] Appl. No.: 413,643

[22] Filed: Sep. 1, 1982

[30] Foreign Application Priority Data

Sep. 4, 1981 [DE] Fed. Rep. of Germany ....... 3135113

[51] Int. Cl.³ .............................................. C08F 2/50
[52] U.S. Cl. .............................. 433/199; 204/159.18; 204/159.24; 430/281; 430/919; 433/217; 433/228
[58] Field of Search ................... 204/159.24; 430/281, 430/919; 204/159.18; 433/199, 228, 217

[56] References Cited

U.S. PATENT DOCUMENTS

| | | | |
|---|---|---|---|
| 3,615,467 | 10/1971 | Poot et al. | 430/919 |
| 4,224,225 | 9/1980 | Noguchi et al. | 430/919 |
| 4,263,393 | 4/1981 | Chen | 430/390 |
| 4,278,750 | 7/1981 | Chen | 430/390 |

FOREIGN PATENT DOCUMENTS 737796 7/1943 Fed. Rep. of Germany.

OTHER PUBLICATIONS

Kumler; Journal of the Amer. Chem. Soc. 68 (1946), pp. 1184–1192.
Chem. Abstracts 69:96122q.

Primary Examiner—John C. Bleutge
Assistant Examiner—A. H. Koeckert
Attorney, Agent, or Firm—Sprung, Horn, Kramer & Woods

[57] ABSTRACT

In a photopolymerizable composition comprising
(a) at least one ethylenically unsaturated photopolymerizable monomer.
(b) at least one photoinitiator selected from organic mono- and/or di-carbonyl compounds and
(c) a photoactivator, the improvement which comprises employing as said photoactivator at least one alkylaminoarylsulphonyl compound of the formula

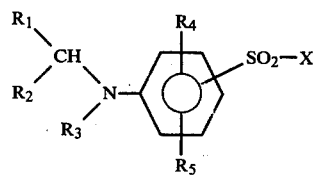

in which
$R_1$ and $R_2$ each independently is a hydrogen atom or an alkyl, alkenyl, cycloalkyl, cycloalkenyl, aryl, aralkyl or alkaryl group which has 1 to 11 carbon atoms and is optionally substituted by at least one hydroxyl, amino, epoxy, urethane, urea, ether of ether group, or $R_1$ and $R_2$ together form a 3- to 6-membered ring, which optionally contains nitrogen, oxygen or sulphur as a hetero-atom,
$R_3$ independently of $R_1$, has any of the meanings given for $R_1$ or is a group of the formula

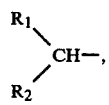

$R_4$ and $R_5$ each independently is a hydrogen atom, an alkyl or alkenyl group which has 1 to 10 carbon atoms and is optionally substituted by halogen, or a halogen atom, or
$R_4$ and $R_5$ are in ortho-positions relative to one another and, together with the aromatic nucleus, form a 4- to 8-membered ring, and
X is an alkyl or alkenyl group which has 1 to 10 carbon atoms and is optionally substituted by a hydroxyl, amino, urethane, urea or ester group, or is a group of the formula

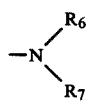

wherein
$R_6$ and $R_7$, independently of $R_1$ and $R_2$, have any of the meanings given above for $R_1$ and $R_2$.

The compositions are especially useful for dental prostheses, fillings and coatings since they are not irritating to human tissue.

13 Claims, No Drawings

PHOTOPOLYMERIZABLE DENTAL COMPOSITIONS

The invention relates to certain photopolymerizable compositions containing at least one ethylenically unsaturated polymerizable monomer and a light-sensitive catalyst system and to their use for dental purposes.

The compositions according to the present invention are particularly suitable for the production of pasty and liquid dental compositions which do or do not contain fillers, of dental prostheses, dental repair materials and dental filling compositions, and of coating and adhesive compositions for dental purposes.

It is known that the polymerization of ethylenically unsaturated monomers which can be polymerized by free radicals can be induced with the aid of radiation energy, such as ultraviolet and/or visible light. Photoinitiators which are transformed into a chemically reactive excited state either by direct absorption of light or by energy transfer from a sensitizer excited by a photochemical route are usually employed for this purpose. The free radicals which trigger off the polymerization are produced either by fragmentation of the excited photoinitiators or by reaction thereof with other molecules, for example hydrogen donors or electron donors, the free radicals which trigger off polymerization being formed from these other molecules. With regard to the absorption of light in the case of photochemically initiated free radical polymerization, the absorption bands of the sensitizers or initiators must as far as possible correspond with the main emission bands of the radiation sources used. The extinction coefficient of the sensitizers and photoinitiators is also important. If the extinction coefficients or the concentrations of the sensitizers, photoinitiators or other additives are too high, only superficial polymerization of the monomers is effected, with the known disadvantages.

The photofragmentable initiators which are in themselves known include, for example, peroxides, azo compounds, α-acyloxime esters, such as 1-phenyl-propane-1,2-dione-2-o-benzoyloxime, and also disulphides, phenylglyoxalates, α-halogenoketones, such as trichloroacetophenone, aromatics carrying halogenomethyl groups, and aryl sulphochlorides. Carbonyl compounds, for example acyloins and benzoin and its derivatives, have achieved particular importance for polymerization with ultraviolet light (in this context, compare, for example, U.S. Pat. No. 2,367,661; H. G. Heine, H. J. Rosenkranz and H. Rudolph, Angewandte Chemie 84, 1032 (1972)). The alkoxy-acetophenone derivatives described in U.S. Pat. No. 3,715,293, such as 2,2-diethoxyacetophenone and benzil dimethyl ketal, and the hydroxyalkylphenones described in DE-OS (German Published Specification) No. 2,808,459, are also very effective.

The second group of photoinitiators, which only trigger off photopolymerization if synergistically effective hydrogen donors or other substances which form free radicals ("radical-generating agents") are simultaneously present, includes the aromatic monoketones of the benzophenone type, such as benzophenone, fluorenone, xanthone, thioxanthone and dibenzosuberone, and also the polynuclear quinones, such as anthraquinone (U.S. Pat. No. 2,989,455), certain oxidizing dyestuffs and 1,2-diketones from the aromatic, cycloaliphatic and aliphatic series, for example phenanthrenequinone, bornane-2,3-dione (U.S. Pat. No. 2,951,758), benzil (U.S. Pat. No. 2,367,660) and diacetyl or dipivaloyl.

The synergistically active compounds mentioned, which are called hydrogen donors, chain transfer agents (U.S. Pat. No. 3,046,127), reducing compounds or, generally, photoactivators (European Published Patent Application No. 2,625), include certain ethers, for example tetrahydrofuran, alcohols, mercaptans, thioethers, alkylphosphines, N-allyl compounds, such as allylthiourea, and, in particular, amines which contain alkyl groups and carry a CH group in the α-position relative to the nitrogen. In this context, compare, for example, M. R. Sandner et al., Journal of Polymer Science, Polymer Chemistry Edition 10 (1972), pages 3173–3181, and also U.S. Pat. No. 3,759,807. Examples of the combination of α-diketones and reducing amines are given in U.S. Pat. Nos. 3,450,613 and 4,071,424 and in DE-OS (German Published Specification) No. 2,003,132 (Example 34).

Aminocarbonyl compounds containing the grouping of the formula

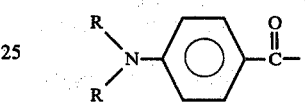

have also been described as photoinitiators.

The best known representative of this group is 4,4'-bis-(dimethylamino)-benzophenone, or Michler's ketone, which is capable of triggering off photopolymerization reactions by itself and also in combination with benzophenone and other carbonyl compounds and peroxides (compare German Patent Specification No. 760,351 and U.S. Pat. No. 3,427,161 and 3,718,473). However, the polymerization products are severely discolored when this compound is used.

DE-OS (German Published Specification) No. 2,458,345, European Published Patent Application No. 2,625 and British Patent Specification No. 1,547,919 propose para- and ortho-dialkylaminobenzoates, as reducing agents (photoactivators) which produce less discoloration in combination with benzophenone or 2-chlorothioxanthone, but the photopolymers thus prepared also still become significantly discolored when they are exposed for a relatively long period.

It is also known to prepare dental compositions which do or do not contain fillers by photopolymerization. German Patent Specification No. 760,351 describes the photopolymerization of plastic mixtures of monomeric and polymeric methacrylates in the presence of benzoyl peroxide and Michler's ketone by the action of UV light and/or heat radiation.

British Patent Specification No. 569,974 describes photopolymerizable dental compositions of monomer/polymer mixtures which contain, as photoinitiators, acyloins, benzoin or polyketaldonyl compounds of the formula R—(CO)$_n$—R$^1$, for example diacetyl, benzil, phenylglyoxal, cyclohexane-1,2-dione, and diphenyl triketone. U.S. Pat. Nos. 3,629,187 and 3,709,866 describe UV-curable dental compositions which contain inorganic fillers. U.S. Pat. Nos. 4,089,763 and 4,110,184 and DE-OS (German Published Specification) No. 2,419,887 describe dental filling materials which contain urethane acrylates, inorganic fillers, α-diketones and unsaturated amines, such as dimethylaminoethyl methacrylate, or other reducing compounds. European Published Patent Application No. 12,535 describes special combinations of urethane acrylates, polymerizable diluents, α-diketones and organic amines, which can be used as photopolymerizable fissure-sealants, adhesion promoters or as orthodontic adhesives.

DE-OS (German Published Specification) No. 2,751,057 and U.S. Pat. No. 4,192,795 describe photopolymerizable dental repair materials which are opaque to X-rays and contain α-diketones (benzil) as photoinitiators and alkylamines, such as dimethylbenzylamine or dimethylparatoluidine, as photoactivators.

Finally, DE-OS (German Published Specification) No. 2,856,550 describes a photopolymerizable, opaque dental filling material which contains 1-20% of the calcium fluoride. Benzil dimethyl ketal or α-methylbenzoinmethyl ether in combination with phosphites or the system phenanthrenequinone/dimethylaminoethyl methacrylate (DMAEM) is used as the photoinitiator. However, DMAEM is known to be highly irritating to human tissue.

According to the present invention we provide a photopolymerizable composition comprising (a) at least one ethylenically unsaturated polymerizable monomer, (b) at least one photoinitator selected from organic mono-and/or di-carbonyl compounds, and (c) at least one aromatic amine as the photoactivator which is an alkylaminoarylsulphonyl compound of the general formula

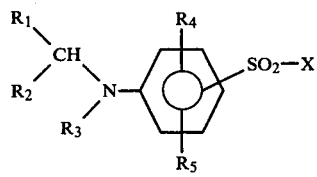
(I)

in which $R_1$ and $R_2$ are identical or different and denote a hydrogen atom or an alkyl, alkenyl, cycloalkyl, cycloalkenyl, aryl, aralkyl or alkaryl group which has 1 to 11 carbon atoms and is optionally substituted by one or more (preferably only one) hydroxyl, amino, epoxy, urethane, urea, ester or ether group, or $R_1$ and $R_2$ together form a 3- to 6-membered ring, which optionally contains nitrogen, oxygen or sulphur as hetero-atoms, $R_3$, independently of $R_1$, has any of the meanings given for $R_1$ or denotes a group of the general formula

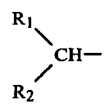

$R_4$ and $R_5$ are identical or different and represent a hydrogen atom, an alkyl or alkenyl group which has 1 to 10 carbon atoms and is optionally substituted by halogen, or a halogen atom, or $R_4$ and $R_5$ in the ortho-position relative to one another, together with the aromatic nucleus, form a 4- to 8-membered ring, and X denotes an alkyl or alkenyl group which has 1 to 10 carbon atoms and is optionally substituted by a hydroxyl, amino, urethane, urea or ester group, or, preferably, denotes a group of the general formula

wherein $R_6$ and $R_7$, independently of $R_1$ and $R_2$, have any of the meanings given above for $R_1$ and $R_2$.

Preferred photopolymerizable compositions according to the present invention comprise, as a further component a fine-particled inorganic filler and/or a fine-particled organic filler.

The present invention further relates to a process for the production of dental prostheses, dental fillings or coatings for teeth, comprising forming the said prostheses, fillings or coatings from a photopolymerizable composition according to the present invention and then polymerizing the said composition under the action of light in a suitable form.

The photoinitiators of component (b) are in themselves known; the following may be mentioned as examples: anthraquinone, 2-ethylanthraquinone, 2-t-butylanthraquinone, 1-chloro-anthraquinone, 1,2-benzoanthraquinone, 2,3-benzoanthraquinone, phenanthrenequinone, benzil, naphthil, furil, 5,12-naphthoquinone, acenaphthenequinone, diacetyl, dipivaloyl, bornane-2,3-dione, 1,1,4,4-tetramethyl-tetralin-2,3-dione, 2,2,5,5-tetramethyl-tetrahydrofuran-3,4-dione, imidazoletrione, isatin, benzophenone, benzophenone-tetracarboxylic acid derivatives, acetophenone, propiophenone, trichloroacetophenone, phenyl cyclopropyl ketone, 1,3-diphenylpropan-2-one, 1,3,5-triacetylbenzene, anthrone, benzanthrone, 4-acetylbiphenyl, benzoylbiphenyl, β-naphthyl phenyl ketone, dibenzosuberone, xanthone, fluorenone, thioxanthone, 2-chlorothioxanthone, 2-benzoylbenzophenone, benzophenone-o-carboxylic acid and derivatives thereof, acridone and its derivatives, and α-diketones.

Preferred α-diketones are phenanthrenequinone and those cycloaliphatic α-diketones which are not capable of intra-molecular abstraction of hydrogen, for example bornane-2,3-dione.

The photoinitiators are preferably used in an amount of 0.001-10% by weight, in particular 0.01-5% by weight, relative to the monomer. The molar ratio of the photoinitiators to photoactivators of the formula (I) can be, for example, 0.01:1 to 10:1. The preferred range is 0.01:1 to 1:1. The photoinitiators and photoactivators can also be employed as mixtures.

Other photoinitiators which do not belong to the group of mono- or di-carbonyl compounds can also additionally be used according to the invention. These photoinitiators include, for example, photoreducible dyestuffs according to U.S. Pat. Nos. 2,850,445, 3,579,339 and 3,495,987. The abovementioned photofragmentable photoinitiators can also be added, for example, in order to extend the usable wavelength range of the radiation sources. Examples of suitable photoinitiators for this purpose are benzil dimethyl ketal, the benzoin ethers, and the hydroxyalkylphenones described in DE-OS (German Published Specification) No. 2,808,459. Other advantageous possible combinations are obtained by using α-diketones together with the alkylaminoarylsulphonyl compounds of the formula (I) and sensitizers according to U.S. Pat. No. 3,756,827. The compounds of the formula (I) can also be used instead of the amines mentioned in German Patent Specification No. 2,625,538, in combination with the mono- and di-carbonyl compounds listed therein.

The reducing photoactivators of the formula (I) to be used, according to the invention, in combination with mono- or di-carbonyl compounds contain, as active structural units, an aminoalkyl group which has at least one hydrogen atom in the α-position relative to the amine nitrogen and is bonded to an aromatic nucleus carrying at least one sulphonyl group $SO_2$—X. The aminoalkyl group is preferably in the meta- or para-position, particularly preferably in the para-position, relative to the sulphonyl group. Any desired substituents $R_1$–$R_5$ and X can be chosen, but $R_1$ and $R_2$ are particularly preferably hydrogen, $R_2$ is particularly preferably also methyl, $R_3$ is particularly preferably methyl, and $R_4$ and $R_5$ are particularly preferably hydrogen. However, in any event, the substituents must not adversely affect the intended use, that is to say must not impair the polymerization or the stability to light. Furthermore, these substituents should ensure sufficient solubility of the activators in the monomers used.

The substituents $R_1$, $R_2$, $R_3$, $R_4$ and $R_5$ which are preferred in compositions according to the invention are the following: $R_1$ and $R_2$: hydrogen, methyl, vinyl and phenyl; $R_3$: hydrogen, methyl and ethyl; $R_4$ and $R_5$: hydrogen, halogen and methyl; or $R_4$ and $R_5$ in the ortho-position relative to one another: members of a fused-on 6-membered aromatic ring; $R_6$ and $R_7$: hydrogen, alkyl (preferably methyl), allyl, methallyl, cyclohexyl, phenyl, benzyl, hydroxyethyl, hydroxypropyl, acryloxyalkyl, methacryloxyalkyl, 2,3-epoxypropyl and 1,2-dihydroxypropyl-1-(meth)acrylate; and X:

for example a morpholine or piperidine group.

The activators preferably contain, as the substituent —$SO_2$—X, a sulphone group or, particularly preferably, a sulphonamide group with aliphatic, cycloaliphatic or heterocyclic substituents. Another preferred series includes alkylaminoaryl-sulphonamides or -sulphones which contain polymerizable groups, for example allyl groups, as well as (meth)acrylate groups or maleate groups, which can easily be introduced into compounds of the general formula (I) containing hydroxyalkyl or ethoxyalkyl groups by methods which are in themselves known. Suitable intermediates for this purpose are the compounds 1a, 7, 10 and 12 listed in Table 1 below. A further possibility of introducing polymerizable groups into compounds of formula (I) is the reaction of alkylaminoarylsulphonyl compounds of the formula (I) which carry hydroxyl groups or amino groups with unsaturated isocyanates or unsaturated urethane prepolymers carrying isocyanate groups. Photocatalysts of the formula (I) where X is the group

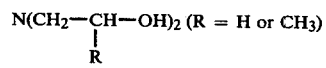

can advantageously be condensed into the polyester by a method analogous to that in German Patent Specifications Nos. 919,431 and 1,942,954. Compounds of the formula (I) in which X is the group

can be reacted with N-methoxymethyl-acrylamide or -methacrylamide to give unsaturated photoactivators in which X denotes

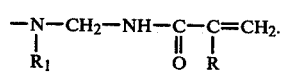

Thus particularly preferably, photoactivators of formula (I) contain in the radical X at least one hydroxyl, epoxy or ethylenically unsaturated group; and X especially represents a radical of the general formula

which contains at least one allyl, acrylamide, methacrylamide, acrylate or methacrylate group.

Since such polymerizable or co-condensed photoactivators of the formula (I) incorporated are built into the polymer matrix, they are particularly suitable for photopolymerizable compositions which come into contact with the human body, for example for use as bone cements, dental cements, dental filling compositions and sealing compositions. As a result of their low basicity, they do not irritate tissue and are therefore superior to other polymerizable reducing photoactivators, such as, for example, dimethylaminoethyl methacrylate (DMAEM), which, as an aliphatic amine, is highly irritating to tissue.

The alkylaminosulphonyl compounds of the formula (I) are prepared by methods which are in themselves known, such as those described, for example, in Houben-Weyl, "Methoden der organischen Chemie" ("Methods of organic chemistry"), Georg Thieme Verlag 1955, volume IX, pages 227 et seq. and 606 et seq.

Many compounds which are suitable as precursors are described, for example, in E. M. Northey, "The sulfonamides and allied compounds", Reinhold Publishing Corporation, New York 1948.

The compounds listed in Table 1 which follows, some of which are new, can, for example, be used (see the examples hereinbelow):

TABLE 1

| Compound No. | Formula | Melting point (°C.) |
|---|---|---|
| 1 (J.A.C.S. 68, (1946), 1184, 1191) | 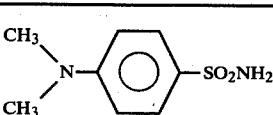 | 210–212 |

TABLE 1-continued

| Compound No. | Formula | Melting point (°C.) |
|---|---|---|
| 1a | (CH₃)₂N–C₆H₄–SO₂NH–CH₃ | 142 |
| 2 | (CH₃)₂N–C₆H₄–SO₂N(CH₃)–CH₂–CH(–O–)CH₂ (epoxide) | 85–86 |
| 3 | CH₃(H)N–C₆H₄–SO₂NH–CH₂–CH=CH₂ | 91–93 |
| 4 (preferred) | (CH₃)₂N–C₆H₄–SO₂NH–CH₂–CH=CH₂ | 111–112 |
| 5 | (C₂H₅)₂N–C₆H₄–SO₂–NH–CH₂–CH=CH₂ | 87–88 |
| 6 (preferred) | (CH₃)₂N–C₆H₄–SO₂–N(CH₂–CH=CH₂)₂ | 75 |
| 7 (preferred) | (CH₃)₂N–C₆H₄–SO₂NH–CH₂–CH₂–OH | 104–106 |
| 7a (preferred) | (CH₃)₂N–C₆H₄–SO₂N(CH₂–CH₂–OH)₂ | |
| 8 (preferred) | (CH₃)₂N–C₆H₄–SO₂NH–CH₂–CH₂–O–C(=O)–C(CH₃)=CH₂ | 122 |
| 9 (preferred) | (CH₃)₂N–C₆H₄–SO₂–NH–CH₂–CH₂–O–C(=O)–CH=CH₂ | 89 |
| 10 (U.S. Pat. Specification No. 3,337,592 Example 2) | (CH₃)₂N–C₆H₄–SO₂N(CH₃)–CH₂–CH₂–OH | 90 |
| 11 (C.A. 69, 96122 q) | (CH₃)₂N–C₆H₄–SO₂N(morpholino: –CH₂–CH₂–O–CH₂–CH₂–) | 202–204 |

TABLE 1-continued

| Compound No. | Formula | Melting point (°C.) |
|---|---|---|
| 12 | (CH$_3$)$_2$N—C$_6$H$_4$—SO$_2$—CH$_2$—CH$_2$—OH | 102–103 |
| 13 | 3-(N(CH$_3$)$_2$)-C$_6$H$_4$—SO$_2$NH—CH$_2$—CH=CH$_2$ | 71–72 |
| 14 | 3-(N(C$_2$H$_5$)$_2$)-C$_6$H$_4$—SO$_2$—NH—CH$_2$—CH=CH$_2$ | 60–61 |
| 15 | 3-(N(CH$_3$)$_2$)-C$_6$H$_4$—SO$_2$—N(CH$_2$—CH=CH$_2$)$_2$ | 23–24 |
| 16 | 3-(N(CH$_3$)$_2$)-C$_6$H$_4$—SO$_2$—NH—C$_6$H$_5$ | 115–117 |
| 17 | 3-(N(CH$_3$)$_2$)-C$_6$H$_4$—SO$_2$—N(CH$_3$)—C$_6$H$_5$ | 137–144 |
| 18 | 3-(N(CH$_3$)$_2$)-C$_6$H$_4$—SO$_2$—N(CH$_2$CH$_2$)$_2$O (morpholino) | 123–124 |

TABLE 1-continued

| Compound No. | Formula | Melting point (°C.) |
|---|---|---|
| 19 | phenyl with SO₂NH—CH₂—CH₂—OH and N(CH₃)₂ substituents | 99–100 |
| 20 | phenyl with SO₂N(CH₃)₂ and N(CH₃)₂ substituents | 53–54 |
| 21 | phenyl with SO₂N(CH₃)₂ and NH—CH₃ substituents | 81 |
| 22 | phenyl with SO₂NH—CH₂—CH₂—OH and NH—CH₃ substituents | 128–130 |
| 23 (German Patent Specification 737,796) | (CH₃)₂N—phenyl—SO₂N(CH₃)—pyridyl | 155 |

The monomers contained in the compositions according to the invention contain at least one double bond which can be polymerized by free radicals. Monomers containing more than one double bond and having a boiling point above 100° C. under 13 mbar are preferably used. Highly crosslinked polymers or copolymers are thereby obtained. The molecular weights of the monomers can be between about 70 and 20,000, preferably between about 150 and 1,000. The viscosity of the monomers can be adjusted by suitable mixing of more highly viscous or higher-molecular monomers with low-viscosity monomers. To establish the transparency of dental compositions according to U.S. Pat. No. 3,066,112 which contain a large amount of filler, it is necessary to match the refractive index of the polymers with the refractive index of the fillers. Where relevant, the monomers contain small amounts of polymerization inhibitors, such as, for example, 0.01–0.2% of 2,6-di-t-butyl-p-cresol.

Examples of possible monomers are: esters of unsaturated mono- or di-carboxylic acids, for example esters of acrylic, methacrylic, α-cyanoacrylic, crotonic, cinnamic, sorbic, maleic, fumaric or itaconic acid with aliphatic, cycloaliphatic or aromatic-aliphatic monohydric to tetrahydric alcohols having 2–30 carbon atoms, for example methyl (meth)acrylate, n-, i- or t-butyl (meth)acrylate, 2-ethylhexyl acrylate, lauryl acrylate, dihydrodicylcopentadienyl (meth)acrylate, dihydroxymethyl-tricyclo[5,2,1,0$^{2,6}$]decane di(meth)acrylate according to German Patent Specification No. 2,200,021, methylglycol di(meth)acrylate, hydroxyethyl (meth)acrylate, hydroxypropyl (meth)acrylate, ethylene glycol diacrylate, diethylene glycol diacrylate, triethylene glycol di(meth)acrylate, neopentylglycol di(meth)acrylate, 1,4-dimethylolcyclohexane diacrylate, pentaerythritol tri- or tetra(meth)acrylate, trimethylolpropane tri(meth)acrylate, ethyl α-cyanoacrylate, ethyl crotonate, ethyl sorbate, diethyl maleate, diethyl fumarate, the di(meth)acrylate of oxyalkylated bisphenol A according to U.S. Pat. Nos. 3,810,938 and 3,923,740, di(meth)acrylates of oxyalkylated trimethylolpropane or pentaerythritol according to U.S. Pat. No. 3,380,831, and the (meth)acrylates of oxyalkylated di(hydroxymethyl)-tricyclo[5,2,1,0$^{2,6}$]-decanes, such as are described in DE-OS (German Published Specification) No. 2,931,925 and DE-OS (German Published Specification) No. 2,931,926.

Other monomers which can be used according to the invention are amides of (meth)acrylic acid, which can optionally be substituted on the nitrogen atom by alkyl, alkoxyalkyl or hydroxylalkyl groups such as, for example, N-isobutylacrylamide, diacetone-acrylamide, N-methylolacrylamide, N-methoxymethylacrylamide, N-butoxymethyl-methacrylamide, ethylene glycol bis-(N-methylolacrylamide) ether and methylene-bis-acrylamide; triacrylformal; vinyl esters of mono- or di-carboxylic acids having 2 to 20 carbon atoms, for example vinyl acetate, vinyl propionate, vinyl 2-ethylhexanoate, vinyl versatate and divinyl adipate; vinyl ethers of monohydric or dihydric alcohols having 3 to 20 carbon atoms, for example isobutyl vinyl ether, octadecyl vinyl ether, ethylene glycol divinyl ether and diethylene glycol divinyl ether; mono-N-vinyl compounds, for example N-vinylpyrrolidone, N-vinylpiperidone, N-vinylcaprolactam, N-vinylmorpholine, N-vinyloxazolidone, N-vinylsuccinimide, N-methyl-N-vinylformamide and N-vinylcarbazole; allyl ethers and esters, for example trimethylolpropane-diallyl ether, trimethylolpropane-triallyl ether, allyl (meth)acrylate, diallyl maleate and diallyl phthalate and its prepolymers; and unsaturated polyesters having molecular weights between 500 and 10,000, if appropriate diluted with styrene or acrylates.

The epoxide acrylates and urethane acrylates are of particular importance for the preparation of photopolymerizable dental compositions. Examples of such compounds which may be mentioned are: (a) reaction products of monofunctional epoxides and (meth)acrylic acids according to U.S. Pat. No. 2,484,487 and U.S. Pat. No. 2,575,440; (b) reaction products of bifunctional epoxides and unsaturated fatty acids according to U.S. Pat. No. 2,456,408; (c) reaction products of polyfunctional aromatic or aliphatic glycidyl ethers and (meth)acrylic acid according to U.S. Pat. Nos. 3,179,623, 3,066,112 and 2,824,851 and German Patent Specification No. 1,644,817; (d) reaction products of epoxide resins and (meth)acrylyl chloride according to U.S. Pat. No. 3,427,161 and U.S. Pat. No. 2,890,202; and (e) unsaturated polyurethanes (urethane acrylates) and polyureas of hydroxyalkyl (meth)acrylates, aminoalkyl (meth)acrylates and, if appropriate, polyols or polyamines, such as are described, for example, in U.S. Pat. Nos. 3,425,988, 3,709,866, 3,629,187, 4,089,763 and 4,110,184 and German Patent Specifications Nos. 1,644,798 and 1,644,797 and DOS (German Published Specification) Nos. 2,357,402, 2,357,324 and 3,358,948.

Other examples of suitable comonomers can be found in the summary which follows; in the structural formulae, R represents

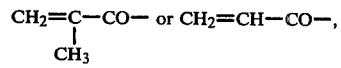

R' represents H or —CH$_2$—OR
n represents an integer from 1 to 4 and
m represents O or an integer from 1 to 4.

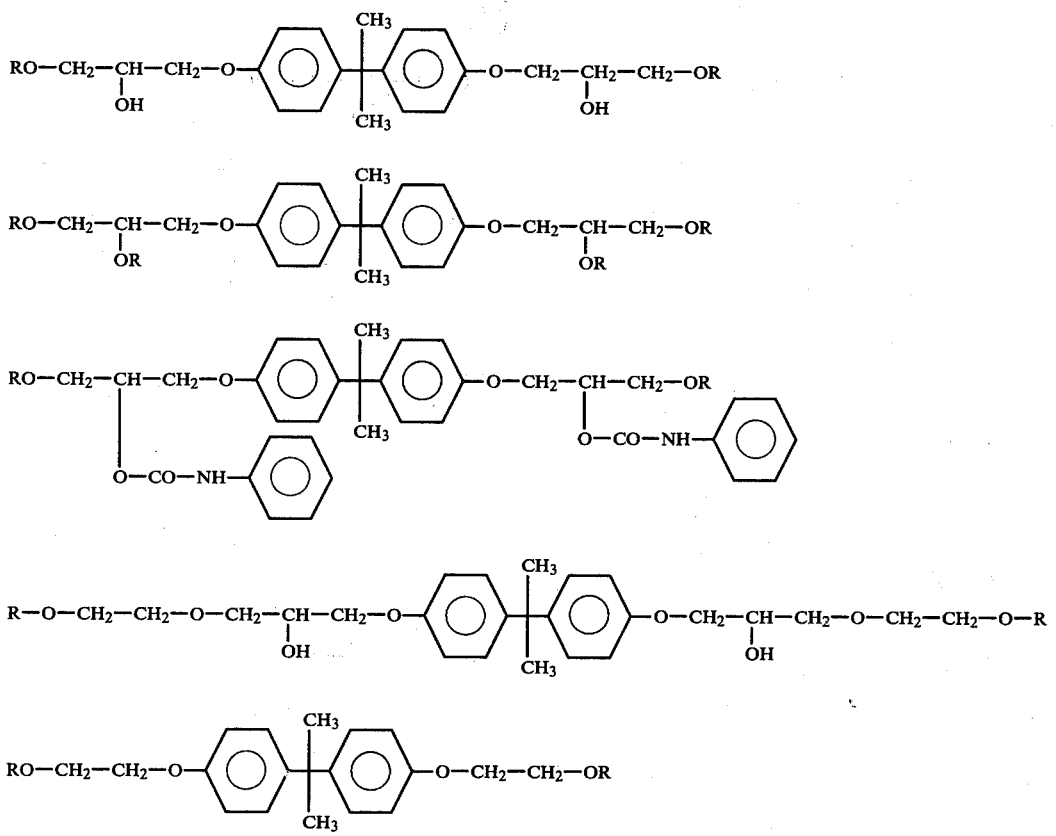

-continued
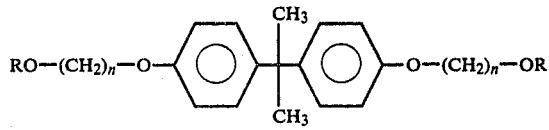
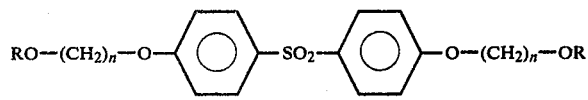
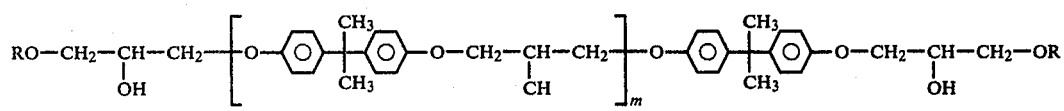
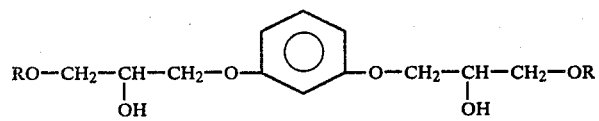
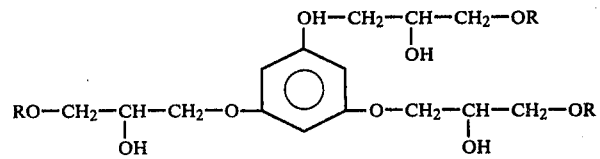
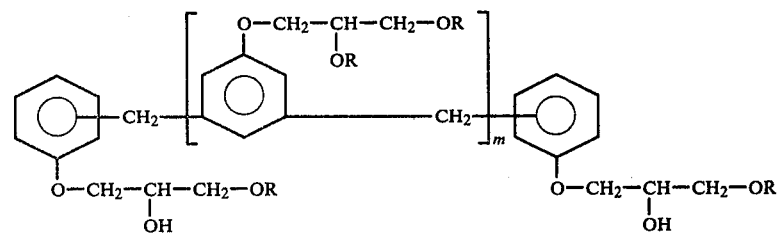
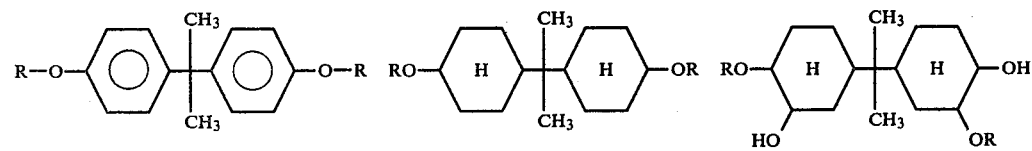
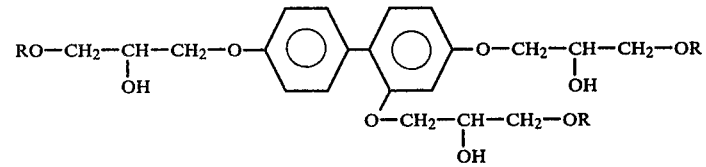
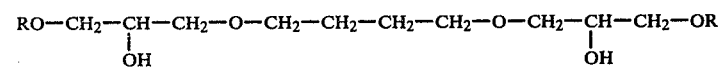
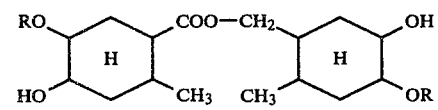

-continued
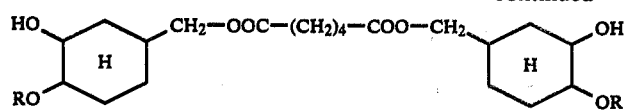
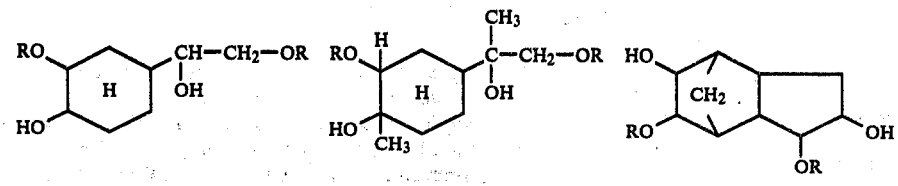
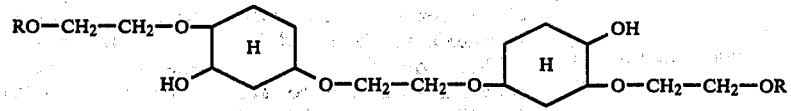
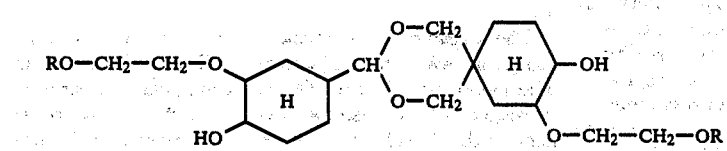
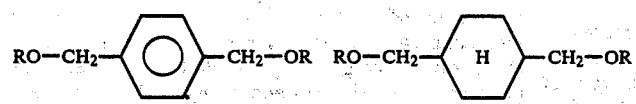
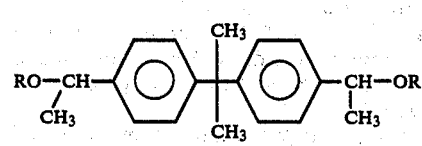
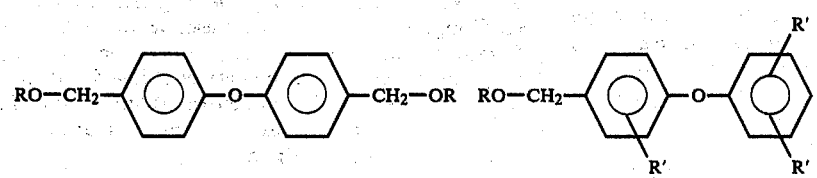
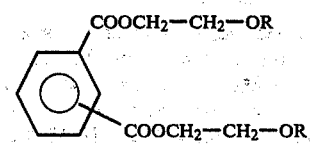
in the ortho-, meta- or para-form
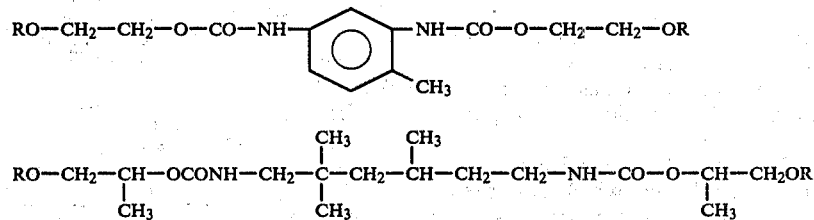

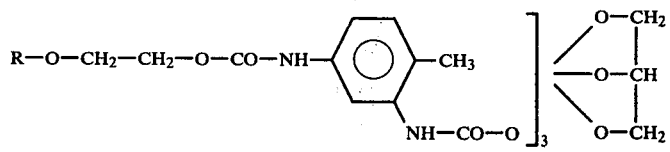

and compounds of the general formula

R—(O—D—O—X)$_n$—OD—OR wherein

HO—D—OH represents a polyol and

HO—X—OH represents a dicarboxylic acid, each of which can be saturated or unsaturated and cyclic or acyclic.

Depending on the intended use, the photopolymerizable compositions, according to the invention, of monomers, photoinitiators and photoactivators can also be additionally admixed with other substances, such as, for example, inorganic and/or organic fillers and pigments, stabilizers, dyestuffs, special light stabilizers, fluorescence agents, plasticizers and soluble, swellable or insoluble high-molecular compounds.

A low-viscosity to pasty consistency of the mixtures of photoactivated monomers and fine-particled fillers is particularly desirable if the photopolymerizable compositions according to the invention are used in the dental field, for example for the production of dental repair materials, dental prostheses and sealing compositions, a sufficient depth of polymerization being required, in spite of the use of inorganic and/or organic fillers. The particle size of the fillers can be, for example, between 10 nm and about 50 μm.

The amount of fillers is preferably 10 to 85% by weight, in particular 40 to 80% by weight, relative to the photopolymerizable monomer. In some cases, for example in the use as sealing compositions, it is not absolutely necessary to add a filler.

Examples of possible inorganic fillers are metal oxides, silicates, phosphates, sulphates, carbonates and fluorides. Specific examples which may be mentioned are: rock crystal, quartzite, novaculite, cristobalite, quartz glass, highly disperse silicic acid, aluminum oxide, zirconium dioxide, titanium dioxide, barium sulphate, calcium fluoride, barium or calcium silicates, β-eucryptite, spodumene, borosilicate glasses and glass ceramics, for example those based on μ-cordierite and glass ceramics containing lanthanum and zirconium, according to DE-OS (German Published Specification) No. 2,347,591.

The inorganic fillers are preferably pre-treated with an adhesion promoter in a manner which is in itself known, in order to increase the bonding to the polymer matrix. Silanes, such as trimethoxy-(3-methacrylyloxypropyl)-silane, or titanates are particularly suitable for this process.

Examples of organic fine-particled fillers which are used are polymers which have been prepared by polymerization of vinyl monomers, graft polymerization, polyaddition or polycondensation. Vinyl polymers which have been prepared by bulk, suspension, emulsion or precipitation polymerization are generally used. Suspension (bead) polymers or polymer chips produced by grinding are preferably used for dental compositions.

The degree of swelling of the polymers can be reduced by copolymerization of polyfunctional monomers.

Examples of suitable polymers which may be mentioned are homopolymers or copolymers of (meth)acrylates, such as methyl methacrylate, ethyl acrylate, isobutyl methacrylate, dodecyl methacrylate, ethylene glycol dimethacrylate, triethylene glycol dimethacrylate, bisphenol diglycidyl dimethacrylate and dodecane-1,12-diol dimethacrylate. Polymers which have been obtained according to DE-OS (German Published Specification) No. 2,849,280 are also particularly suitable.

The organic fine-particled fillers can also contain inorganic microfine substances in finely divided form. The use of such hybrid fillers gives certain advantages in respect of the ease of polishing and abrasion-resistance of the dental materials prepared therefrom. Hybrid fillers can be obtained as polymer chips by bulk polymerization of mixtures of the monomer and microfine inorganic substances and subsequent comminution of the product by grinding. Such hybrid fillers can be prepared in bead form according to DE-OS (German Published Specification) No. 2,849,936.

The examples which follow serve to illustrate the present invention in more detail. Unless indicated otherwise, amounts are to be understood as parts by weight or percentages by weight.

Commercially available dental lamps with a light guide such as are used for photopolymerization of dental fillings in the mouth were used as the light source. Lamps S and U were low-pressure mercury vapor lamps from which only the lines at 365, 405 and 436 nm were used, by insertion of suitable filters. Lamps E, T and F were halogen lamps with emission maxima at 444 (E), 462 (T) and 472 (F) nm.

EXAMPLE 1

The amounts of photoactivator given in Table 2 (the structural formulae of the activators can be found in Table 1) are added to a 0.2% strength solution of bornane-2,3-dione (camphor quinone) in a mixture of 67 parts of BIS-GMA* and 33 parts of **TEGDM. Pastes consisting of in each case 25 parts of the photoactivated monomer mixture and 75 parts of silanized fine-particled glass ceramic based on μ-cordierite are prepared in a ball mill; photopolymerization is effected by means of lamp E (blue light with a low UV content).

*BIS-GMA=2,2-propane-bis[3-(4-phenoxy)-1,2-dihydroxypropane 1-methacrylate]**TEGDM=triethylene glycol dimethacrylate

TABLE 2

| Compound from Table 1 | %, relative to the monomer | Depth of hardening in mm, after an exposure time of | |
|---|---|---|---|
| | | 20 seconds | 40 seconds under lamp E |
| 1 | saturated | 7.0 | 7.7 |
| 18 | 1.35 | 7.2 | 8.5 |
| 17 | 1.45 | 7.5 | 8.6 |
| 16 | 1.38 | 6.9 | 8.0 |
| 11 | saturated | 7.5 | 8.7 |
| 4 | 1.2 | 7.1 | 8.1 |
| 5 | 1.34 | 6.3 | 7.5 |

TABLE 2-continued

| Compound from Table 1 | %, relative to the monomer | Depth of hardening in mm, after an exposure time of | |
|---|---|---|---|
| | | 20 seconds | 40 seconds under lamp E |
| 13 | 1.2 | 6.7 | 8.0 |
| 14 | 1.34 | 5.8 | 7.0 |
| 12 | 1.15 | 7.0 | 8.4 |

EXAMPLE 2

0.01% of 2-chlorothioxanthone and the amounts of photoactivator given in Table 3 are dissolved in a 0.2% strength solution of bornane-2,3-dione in the monomer mixture from Example 1. The pastes are prepared as in Example 1 and are hardened using the lamps S (UV), T and F (blue light).

TABLE 3

| Compound from Table 1 | %, relative to the monomer | Depth of hardening in mm after an exposure time of | | | | |
|---|---|---|---|---|---|---|
| | | 20 seconds under lamp S | 40 seconds under lamp S | 20 seconds under lamp T | 40 seconds under lamp T | 20 seconds under lamp F |
| 6 | 1.4 | 5.2 | 6.4 | 6.4 | 7.8 | 5.7 |
| 4 | 1.2 | 5.1 | 6.0 | 6.0 | 7.8 | 6.0 |
| 13 | 1.2 | 4.5 | 5.5 | 6.2 | 7.6 | 5.95 |
| 15 | 1.4 | 4.6 | 5.5 | 6.3 | 7.4 | 5.8 |
| 12 | 1.15 | 5.4 | 6.3 | 6.1 | 7.4 | 5.9 |
| 8 | 1.56 | 5.0 | 6.1 | 6.2 | 7.1 | 5.7 |
| 7 | 1.2 | 5.1 | 5.9 | 6.2 | 7.1 | 5.5 |
| 11 | saturated | 4.5 | 5.4 | 6.1 | 7.2 | 5.6 |
| 5 | 1.34 | 4.6 | 5.8 | 5.3 | 6.6 | 5.1 |
| 14 | 1.34 | 3.6 | — | 5.7 | — | 4.6 |
| 18 | 1.35 | 4.7 | 5.3 | 6.1 | 6.9 | — |
| 21 | 1.07 | 2.3 | 3.3 | 2.6 | 4.0 | — |
| 20 | 1.14 | 4.0 | 4.7 | 5.6 | 6.8 | — |
| 22 | 1.15 | 2.3 | 3.1 | 2.1 | 3.1 | — |
| 19 | 1.22 | 4.0 | 4.6 | 5.5 | 6.4 | — |
| DMAEM* | 0.8 | 4.9 | 5.9 | 5.8 | 6.8 | 4.8 |

*Dimethylaminoethyl methacrylate, for comparison. It can be seen that the same molar amounts of the skin-irritant DMAEM are inferior to many photoactivators according to the invention.

EXAMPLE 3

0.025% of phenanthrenequinone and (a) 1.56% of the compound 8 (0.5 mmol/100 g) or (b) 1.5% of dimethylaminoethyl methacrylate (0.96 mmol/100 g), comparison experiment, are dissolved in the monomer mixture from Example 1.

The pastes are prepared as in Example 1 and are hardened using lamps S (UV) and T (blue light).

| Experiment | Compound | Depth of hardening in mm after | | | |
|---|---|---|---|---|---|
| | | 20 seconds under lamp S | 40 seconds under lamp S | 20 seconds under lamp T | 40 seconds under lamp T |
| a | 8 | 3.2 | 4.0 | 3.3 | 4.7 |
| b | DMAEM | 2.7 | 3.6 | 4.1 | 5.4 |

It can be seen that considerably greater molar amounts of the skin irritant dimethylaminoethyl methacrylate are required to achieve about the same depth of hardening.

EXAMPLE 4

0.02% of bornane-2,3-dione and 1.56% of the compound 8, as the photoactivator, and increasing amounts of the UV initiator 1-phenyl-2-hydroxy-2-methyl-butan-1-one are dissolved in the monomer mixture from Example 1. The pastes are prepared analogously to Example 1.

| % of UV initiator, relative to the monomer | Depths of hardening in mm after an exposure times of | | | |
|---|---|---|---|---|
| | 20 seconds under lamp S | 40 seconds under lamp S | 20 seconds under lamp T | 40 seconds under lamp T |
| 0 | 2.3 | 3.1 | 6.0 | 7.0 |
| 0.25 | 4.1 | 4.9 | 5.3 | 6.2 |
| 0.5 | 4.7 | 5.1 | 5.3 | 6.6 |
| 1.0 | 4.94 | 4.7 | 5.7 | 6.6 |
| 2.0 | 4.55 | 5.0 | 5.6 | 6.4 |
| 4.0 | 4.4 | 5.0 | 5.7 | 6.6 |

EXAMPLE 5

0.025% of 1-benzoylamino-4-chloroanthraquinone is dissolved in the monomer mixture from Example 1 and increasing amounts of the compound 8 are added. The pastes are prepared analogously to Example 1.

| % of compound 8 relative to the monomer | Hardening in mm after | |
|---|---|---|
| | 20 seconds under lamp E | 40 seconds under lamp E |
| 0 | 0 | 0 |
| 0.185 | 1.2 | 1.7 |
| 0.39 | 1.5 | 2.3 |
| 0.78 | 1.9 | 3.0 |
| 1.04 | 2.2 | 3.2 |
| 1.56 | 2.6 | 3.4 |

EXAMPLE 6

0.2% of bornane-2,3-dione (camphor quinone), 0.01% of 2-chlorothioxanthone and the amounts of photoactivator given in Table 4 are dissolved in a monomer mixture of 67 parts of BIS-GMA and 33 parts of TEGDM which is stabilized with 0.1% of 2,6-di-t-butyl-p-cresol.

98 g of silanized silicon dioxide with a BET surface area of 50 m$^2$/g (silanized with 7.5% of γ-methacrylyloxypropyltrimethoxysilane), 140 g of a bead polymer which has an average particle size of 90μ and has been prepared according to DE-OS (German Published Specification) No. 2,849,936 by polymerization of 28% of silicon dioxide (BET surface area: 50 m$^2$/g), 50% of methylmethacrylate, 18% of isobutyl methacrylate and 4% of BIS-GMA, 1.1 mg of Paliogen Red and 7.2 mg of Irgazine Yellow are added to 100 g of the activated monomer mixture and the components are mixed intensively, while cooling, in a kneader for 30 minutes, a quinone) and 2.4 g of 4-(N,N-dimethylamino-)benzenesulphonic acid hydroxyethylamide (compound 7) are dissolved in 200 g of bis-β-methacryloxy-ethoxymethyl-tricyclo-[5.2.0.1.$^{2.6}$]-decane,

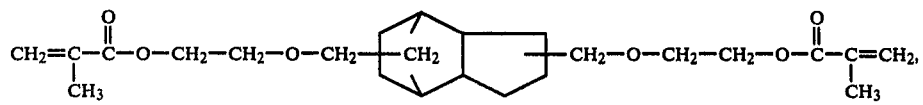

vacuum of 13 mbar being applied during the last 10 minutes.

The pastes are hardened with lamps U and T, and a material with a tooth-colored appearance is thereby formed.

prepared according to DE-OS (German Published Specification) No. 2,931,925).

PASTE A

A paste is prepared from 97 g of activated monomer

TABLE 4

| Compound | %, relative to the monomer | Depth of hardening (mm) after 10 30 60 seconds under lamp U | Depth of hardening (mm) after 10 30 60 seconds under lamp T | Opacity according to ADA 27 | Diametral tensile strength according to ADA 27 (MPa) |
|---|---|---|---|---|---|
| DMAEM* | 1.5 | 1.8 2.8 3.4 | 3.2 4.6 5.2 | 0.36 | 37.43 |
| 6 | 1.4 | 2.3 3.0 3.7 | 3.4 4.7 5.6 | 0.36 | 40.26 |
| 7 | 1.2 | 2.2 3.0 3.6 | 3.3 4.5 5.4 | 0.38 | 41.40 |
| 8 | 1.55 | 2.3 3.2 3.8 | 3.6 4.8 5.5 | 0.37 | 42.60 |

*Comparison example

EXAMPLE 7

To prepare an activated monomer solution, 0.01 g of 2-chlorothioxanthone, 0.2 g of bornane-2,3-dione (camphor quinone) and 1.2 g of 4-(N,N-dimethylamino)-benzenesulphonic acid hydroxyethylamide (compound 7) are dissolved in 100 g of the urethane dimethacrylate prepared by reacting 1 mol of 2,2,4-trimethylhexamethylene diisocyanate and 2 mols of 2-hydroxyethyl methacrylate.

Furthermore, to prepare polymer chips, a mixture of 120 g of the urethane dimethacrylate described above, 20 g of triethylene glycol dimethacrylate and 200 g of silanized silicon dioxide (BET surface area of 50 m$^2$/g, silanized with 10% of γ-methacryloxypropyltrimethoxysilane) is bulk-polymerized by addition of 0.5 g of benzoyl peroxide at 100° C., and the resulting polymerized mass is ground to a mean particle size of 40 μm in a ball mill.

A paste is prepared from 91 g of activated monomer solution, 145 g of polymer chips, 82 g of silicon dioxide (BET surface area of 50 m$^2$/g, silanized with 10% of γ-methacryloxypropyltrimethoxysilane), 0.7 mg of Paliogen Red and 4.3 g of Irgazine Yellow by the procedure described in Example 6.

The paste is hardened using lamps U and T, and a material with a tooth-colored appearance is obtained.

| Depth of hardening [mm] after 20 60 seconds under lamp U | Depth of hardening [mm] after 20 60 seconds under lamp T | Opacity according to ADA 27 | Diametral tensile strength according to ADA 27 [MPa] |
|---|---|---|---|
| 2.5 3.8 | 4.5 5.5 | 0.39 | 39.80 |

EXAMPLE 8

To prepare an activated monomer solution, 0.02 g of chlorothioxantone, 0.4 g of bornane-2,3-dione (camphor solution, 150 g of silicon dioxide (BET surface area of 50 m$^2$/g) silanized with 10% of γ-methacryloxypropyltrimethoxysilane), 0.5 mg of Paliogen Red and 3.2 mg of Irgazine Yellow by the procedure described in Example 6.

PASTE B

A paste is prepared in a corresponding manner from 80 g of activated monomer solution, 120 g of a bead polymer which has a mean particle size of 40μ and has been prepared from 60% of methyl methacrylate, 30% of isobutyl methacrylate and 10% of bis-β-methacryloxyethoxymethyl-tricyclo-[5.2.0.1.$^{2.6}$]-decane, 0.65 mg of Paliogen Red and 4.1 mg of Irgazine Yellow.

Pastes A and B are hardened with lamps U and T, and a material with a tooth-colored appearance is formed.

| | Depth of hardening [mm] After 20 60 seconds under lamp U | Depth of hardening [mm] after 20 60 seconds under lamp T | Opacity according to ADA 27 | Diametral tensile strength according to ADA 27 [MPa] |
|---|---|---|---|---|
| Paste A | 4.0 4.8 | 6.5 7.4 | 0.35 | 43.25 |
| Paste B | 3.9 4.5 | 5.6 7.1 | 0.43 | 35.12 |

It will be appreciated that the instant specification and examples are set forth by way of illustration and not limitation, and that various modifications and changes may be made without departing from the spirit and scope of the present invention.

We claim:
1. A photopolymerizable composition comprising
   (a) at least one ethylenically unsaturated photopolymerizable monomer,

(b) at least one photoinitiator selected from organic mono- or di-carbonyl compounds and
(c) as a photoactivator at least one alkylaminoarylsulphonyl compound of the formula

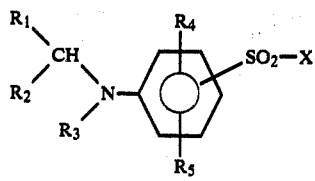

in which

R₁ and R₂ each independently is a hydrogen atom or an alkyl, alkenyl, cycloalkyl, cycloalkenyl, aryl, aralkyl or alkaryl group which has 1 to 11 carbon atoms and is optionally substituted by at least one hydroxyl, amino, epoxy, urethane, urea, ester or ether group, or R₁ and R₂ together form a 3- to 6-membered ring, which optionally contains nitrogen, oxygen or sulphur as a hetero-atom, R₃ independently of R₁, has any of the meanings given for R₁ or is a group of the formula

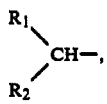

R₄ and R₅ each independently is a hydrogen atom, an alkyl or alkenyl group which has 1 to 10 carbon atoms and is optionally substituted by halogen, or a halogen atom, or R₄ and R₅ are in ortho-positions relative to one another and, together with the aromatic nucleus, form a 4- to 8-membered ring, and X is an alkyl or alkenyl group which has 1 to 10 carbon atoms and is optionally substituted by a hydroxyl, amino, urethane, urea or ester group, or is a group of the formula

wherein

R₆ and R₇, independently of R₁ and R₂, have any of the meanings given above for R₁ and R₂.

2. A composition according to claim 1, containing as a further component at least one fine-particled filler.

3. A composition according to claim 1, in which R₁ is a hydrogen atom or a methyl group.

4. A composition according to claim 1, in which R₂ is a hydrogen atom.

5. A composition according to claim 1, in which R₃ is a methyl group.

6. A composition according to claim 1, in which R₄ and R₅ each is hydrogen.

7. A composition according to claim 1, in which X contains at least one, hydroxyl, epoxy or ethylenically unsaturated group.

8. A composition according to claim 1, in which X is a radical of the formula

and contains at least one allyl, acrylamide, methacrylamide, acrylate or methacrylate group.

9. A composition according to claim 1 in which the moiety containing radicals R₁ to R₃ is in the meta- or para-position to the —SO₂X group.

10. A composition according to claim 2, in which
R₁ is a hydrogen atom or a methyl group,
R₂ is a hydrogen atom,
R₃ is a methyl group, and
R₄ and R₅ each is hydrogen.

11. In a photopolymerizable composition comprising
(a) at least one ethylenically unsaturated photopolymerizable monomer,
(b) at least one photoinitiator selected from organic mono- or di-carbonyl compounds and
(c) a photoactivator, the improvement which comprises employing as said photoactivator at least one alkylaminoarylsulphonyl compound of the formula

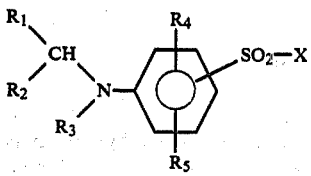

in which

R₁ and R₂ each independently is a hydrogen atom or an alkyl, alkenyl, cycloalkyl, cycloalkenyl, aryl, aralkyl or alkaryl group which has 1 to 11 carbon atoms and is optionally substituted by at least one hydroxyl, amino, epoxy, urethane, urea, ester or ether group, or R₁ and R₂ together form a 3- to 6-membered ring, which optionally contains nitrogen, oxygen or sulphur as a hetero-atom, R₃ independently of R₁, has any of the meanings given for R₁ or is a group of the formula

R₄ and R₅ each independently is a hydrogen atom, an alkyl or alkenyl group which has 1 to 10 carbon atoms and is optionally substituted by halogen, or a halogen atom, or R₄ and R₅ are in ortho-positions relative to one another and, together with the aromatic nucleus, form a 4- to 8-membered ring, and X is an alkyl or alkenyl group which has 1 to 10 carbon atoms and is optionally substituted by a hydroxyl, amino, urethane, urea or ester group, or is a group of the formula

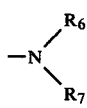

wherein
$R_6$ and $R_7$, independently of $R_1$ and $R_2$, have any of the meanings given above for $R_1$ and $R_2$.

12. A composition according to claim 11, wherein (b) is present in about 0.001 to 10% by weight of (a) and the molar ratio of (b) to (c) is from about 0.01:1 to 10:1.

13. In the formation of a dental prosthesis, filling or coating comprising forming a composition comprising
 (a) at least one ethylenically unsaturated photopolymerizable monomer,
 (b) at least one photoinitiator selected from the organic mono- or di-carbonyl compounds and
 (c) a photoactivator,
 shaping said composition and then polymerizing said composition under the influence of light, the improvement which comprises employing as said photoactivator at least one alkylaminoarylsulphonyl compound of the formula

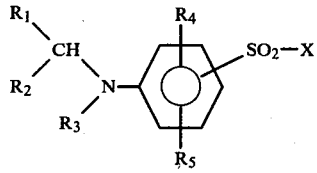

in which
$R_1$ and $R_2$ each independently is a hydrogen atom or an alkyl, alkenyl, cycloalkyl, cycloalkenyl, aryl, aralkyl or alkaryl group which has 1 to 11 carbon atoms and is optionally substituted by at least one hydroxyl, amino, epoxy, urethane, urea, ester or ether group, or $R_1$ and $R_2$ together from a 3- to 6-membered ring, which optionally contains nitrogen, oxygen or sulphur as a hetero-atom,
$R_3$ independently of $R_1$, has any of the meanings given for $R_1$ or is a group of the formula

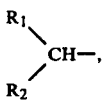

$R_4$ and $R_5$ each independently is a hydrogen atom, an alkyl or alkenyl group which has 1 to 10 carbon atoms and is optionally substituted by halogen, or a halogen atom, or
$R_4$ and $R_5$ are in ortho-positions relative to one another and, together with the aromatic nucleus, form a 4- to 8-membered ring, and
X is an alkyl or alkenyl group which has 1 to 10 carbon atoms and is optionally substituted by a hydroxyl, amino, urethane, urea or ester group, or is a group of the formula

wherein
$R_6$ and $R_7$, independently of $R_1$ and $R_2$, have any of the meanings given above for $R_1$ and $R_2$.

* * * * *

UNITED STATES PATENT AND TRADEMARK OFFICE
CERTIFICATE OF CORRECTION

PATENT NO. : 4,437,836
DATED : March 20, 1984
INVENTOR(S) : Robert Schmitz-Josten et al It is certified that error appears in the above-identified patent and that said Letters Patent is hereby corrected as shown below:

| | |
|---|---|
| Col. 3, line 14 | After "1-20% of" delete "the" |
| Col. 6, line 55 | Delete "Reinhold" and substitute --Reinhard-- |
| Col. 14, line 31 | Underline "n" to read --$\underline{n}$-- |
| Col. 14, line 32 | Underline "m" to read --$\underline{m}$-- |
| Col. 22, line 5 | Delete "times" and substituted --time-- |
| Col. 28, line 4 | Delete "from" and substitute --form-- |

Signed and Sealed this

Fifth Day of February 1985

[SEAL]

Attest:

DONALD J. QUIGG

Attesting Officer     Acting Commissioner of Patents and Trademarks